United States Patent [19]

Passedouet et al.

[11] 4,058,597
[45] Nov. 15, 1977

[54] ALUMINIUM SALTS OF BETAINE CHLORIDE AND COMPOSITIONS CONTAINING THE SAME

[75] Inventors: André Henri Passedouet, Maisons-Laffite; Robert Pipon, Melle, both of France

[73] Assignee: Rhone-Poulenc Industries, Paris, France

[21] Appl. No.: 665,242

[22] Filed: Mar. 9, 1976

[30] Foreign Application Priority Data

Mar. 11, 1975 France .................................. 75.07555

[51] Int. Cl.² .......................... A61K 7/38; C07F 5/06
[52] U.S. Cl. .............................. 424/68; 260/448.2 R; 260/448 R; 424/47; 424/316; 424/329
[58] Field of Search .................. 424/68, 316, 329, 47; 260/448.2, 448 R

[56] References Cited

U.S. PATENT DOCUMENTS

| | | | |
|---|---|---|---|
| 2,508,787 | 5/1950 | Grote et al. ............................. | 424/68 |
| 2,641,604 | 6/1953 | Maistre et al. ......................... | 260/448 R |
| 3,539,605 | 11/1970 | Oberhofer ............................. | 424/287 X |

OTHER PUBLICATIONS

Brevet Special De Medicament No. 7569M, 1/1970, Serviere, 7 pages.
Chemical Abstracts, 1972, vol. 77, pp. 269–270.

*Primary Examiner*—Dale R. Ore
*Attorney, Agent, or Firm*—Stevens, Davis, Miller & Mosher

[57] ABSTRACT

Aluminum salts of the formula:

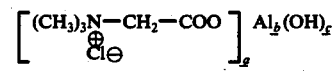

wherein $a$ is an integer from 1 through 4, $b$ is an integer from 1 through 5 and $c$ is an integer from 1 through 13, the numbers represented by the indices $a$, $b$ and $c$ being connected by the relationships $3b = a + c$ and the ratio $b/a$ is equal to or greater than 1 and less than or equal to 2.5, are new compounds possessing pharmacological, anti-perspirant and deodorant properties.

6 Claims, No Drawings

ALUMINIUM SALTS OF BETAINE CHLORIDE AND COMPOSITIONS CONTAINING THE SAME

This invention relates to new aluminium salts useful as pharmaceuticals and in cosmetology, to a process for their preparation and compositions containing them.

The new aluminium salts of this invention are those compounds of the general formula:

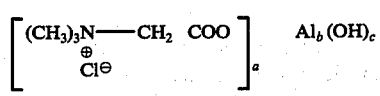   I wherein $a$ represents an integer from 1 to 4 (preferably 1 or 2), $b$ represents an integer from 1 to 5 and $c$ represents an interger from 1 to 13, the numbers represented by the indices $a$, $b$ and $c$ being connected by the relationships $3b = a + c$ and the ratio $b/a$ is equal to or greater than 1 and less than or equal to 2.5. The preferred aluminium salt is that of formula I wherein $a$ is 2, $b$ is 5 and $c$ is 13.

According to a feature of the present invention, the aluminium salts of general formula I are prepared by the process which comprises reacting an aluminium alkoxide with betaine chloride in aqueous solution, the aluminium alkoxide being used in an amount corresponding to the proportion of aluminium in the desired product of general formula I.

Preferably, the aluminium alkoxide used is one obtained from an aliphatic alcohol containing 1 to 3 carbon atoms, such as aluminium methoxide, ethoxide or isopropoxide. In its most preferred aspect, a suspension of aluminium isopropoxide in isopropanol is reacted with an aqueous solution of betaine chloride at a temperture between 50° and 80° C. The preferred molar ratio of aluminum isopropoxide to betaine chloride is 2.5:1.0.

The aluminium salts of general formula I obtained according to the aforedescribed process can be isolated from the reaction mixture after concentrating the latter the residue obtained with a poor solvent such as acetone or diethyl ether.

The aluminium salts of general formula I possess useful pharmacological properties coupled with a low toxicity. They are particularly valuable as anti-ulcer agents, as agents which protect the gastro-intestinal mucous membrane, and as agents which protect the liver. They also have a good cicatrizant activity.

In animals the salts of general formula I, used at doses of between 0.25 and 1 g./kg. animal body weight and administered orally, have proved active against gastric ulcers induced experimentally (i) in rats in accordance with the technique of H. Shay et al. Gastroenterology, 5, 43 (1945), or (ii) in guinea-pigs by the administration of histamine in accordance with the technique of W. Anderson and J. Watt, J. Physiol. (London), 147, 52 P (1959).

In mice, the 50% lethal dose ($LD_{50}$) is generally greater than 5 g./kg. animal body weight when administered orally.

Furthermore, the aluminium salts of the present invention have anti-perspirant and deodorant properties which make them particularly useful in cosmetology.

The aluminium salt of general formula I wherein $a$ is 2, $b$ is 5 and $c$ is 13 has proved particularly active.

The following Examples illustrate the preparation of the new aluminium salts of the present invention.

EXAMPLE 1

Aluminium isopropoxide (205.8 g.; 1.005 mole) suspended in anhydrous isopropanol (300 cc.) is added, over the course of 10 minutes, to betaine chloride (61.8 g.; 0.402 mole) dissolved in distilled water (3,000 cc.) at 60° C. After the end of the addition, the reaction mixture is stirred and heated at 60° C. for 3 hours. The isopropanol is then removed by distillation under reduced pressure. After filtering the reaction mixture to remove insoluble impurities, the filtrate is concentrated to dryness under reduced pressure. The white product obtained is taken up several times in diethyl ether, filtered off and then dried under reduced pressure at 40° C. This gives an aluminium salt of betaine chloride (124.6 g.; 0.188 mole) in the form of a white powder corresponding to the formula:

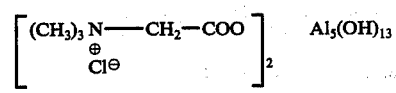   II

Al% = 20.8 (theory = 20.4)

EXAMPLE 2

Following the procedure of Example 1 but starting with betaine chloride (199.5 g.; 1.3 mole) in water (1,300 cc.) and aluminium isopropoxide (266 g.; 1.3 mole) in isopropanol (260 cc.), an aluminium salt of betaine chloride (257 g.) is obtained in the form of a white powder, melting at a temperature above 260° C,. and corresponding to the formula:

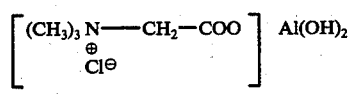   III

The present invention includes within its scope pharmaceutical compositions comprising, as active ingredient, at least one of the salts of general formula I in association with a pharmaceutical carrier or coating. The invention includes especially such preparations made up for oral, parenteral or rectal administration or topical, especially dermal application, e.g. as ointments.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Preparations according to the invention for parenteral administration include sterile aqueous or non-aqueous solutions, suspensions or emulsions.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained.

The compositions according to the invention are particularly useful in human therapy in the treatment of gastrites and various gastralgias induced by other medicines, and in the treatment of ulcerous maladies (gastric or duodenal ulcers and peptic ulcers).

In human therapy, the dosages depend on the desired effect and on the duration of the treatment; they are generally between 1 and 5 g. per day when administered orally to an adult.

In general, the physician will decide the posology considered appropriate, taking into account the age, weight and other factors intrinsic to the patient being treated.

The following Example illustrates pharmaceutical compositions according to the invention.

EXAMPLE 3

Tablets having the following composition are prepared in accordance with the usual technique:

aluminium salt of betaine chloride of formula II depicted hereinbefore: 0.500 g.
starch: 0.150 g.
precipitated silica: 0.095 g.
magnesium stearate: 0.005 g.

The present invention is also concerned with antiperspirant and deodorant cosmetic compositions which comprise at least one of the aluminium salts of general formula I in association with a suitable cosmetic vehicle, and optionally with microbicidal agents.

The compositions can be in various forms and, more particularly, in the form of lotions, creams, powders, milks or aerosols.

In these cosmetic compositions the percentage by weight of the salt(s) of general formula I is genrally between 0.01% and 5%.

The lotions are either aqueous solutions or aqueous-alcoholic solutions which contain between 0.01% and 1% by weight of salt of general formula I.

The creams are emulsions of a mineral, animal or vegetable oil in water which contain between 0.01% and 5% by weight of salt of general formula I.

The compositions when in the form of powders contain between 0.01% and 5% by weight of salt of general formula I mixed with talc and with one or more anti-agglomerating agents.

The compositions, when in a form suitable for use as an aerosol, comprise an aqueous-alcoholic solution of a salt of general formula I and at least one propellant under pressure.

The following Example illustrates a cosmetic composition according to the invention.

EXAMPLE 4

A deodorant and anti-perspirant talc having the following composition is prepared.

aluminium salt of betaine chloride of formula II depicted hereinbefore: 5 g.
magnesium stearate: 5 g.
titanium oxide: 5 g.
salicylic acid; 2 g.
talc: q.s.p. 100 g. We claim:

1. An aluminium salt of the formula:

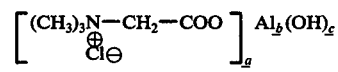

wherein $a$ is an integer from 1 through 4, $b$ is an integer from 1 through 5 and $c$ is an integer from 1 through 13, the numbers represented by the indices $a$, $b$ and $c$ being connected by the relationships $3b = a + c$ and the ratio $b/a$ is equal to or greater than 1 and less than or equal to 2.5.

2. An aluminium salt according to claim 1 wherein $a$ is 1 or 2.

3. An aluminium salt according to claim 1 wherein $a$ is 2, $b$ is 5 and $c$ is 13.

4. An aluminium salt according to claim 1 wherein $a$ is 1, $b$ is 1 and $c$ is 2.

5. Pharmaceutical composition useful as an anti-ulcer agent which comprises, as active ingredient, an effective amount of an aluminium salt of the formula depicted in claim 1, wherein $a$, $b$ and $c$ are as defined in claim 1, in a pharmaceutical carrier.

6. Anti-perspirant or deodorant cosmetic composition which comprises an aluminium salt of the formula depicted in claim 1, wherein $a$, $b$ and $c$ are as defined in claim 1, in a cosmetic vehicle selected from the group consisting of lotion, cream, powder, milk and aerosol, the composition containing from 0.01% to 5% by weight of said aluminium salt.

* * * * *